United States Patent [19]

Garnier et al.

[11] Patent Number: 4,936,966
[45] Date of Patent: Jun. 26, 1990

[54] PROCESS FOR THE ELECTROCHEMICAL SYNTHESIS OF ALPHA-SATURATED KETONES

[75] Inventors: Laurence Garnier, Paris; Yolande Rollin, Boissy Saint Leger; Jacques Perichon, Savigny Sur Orge, all of France

[73] Assignee: Societe Nationale des Poudres et Explosifs, Paris, France

[21] Appl. No.: 286,246

[22] Filed: Dec. 19, 1988

[30] Foreign Application Priority Data

Dec. 18, 1987 [FR] France ............................... 87 17671

[51] Int. Cl.$^5$ ............................................... C25B 3/00
[52] U.S. Cl. ................................... 204/59 R; 204/72; 204/78; 204/79
[58] Field of Search .................. 204/59 R, 72, 78, 79, 204/80

[56] References Cited

U.S. PATENT DOCUMENTS

| | | | |
|---|---|---|---|
| 4,582,577 | 4/1986 | Wagenknecht | 204/59 R |
| 4,601,797 | 7/1986 | Wagenknecht | 204/59 R |
| 4,629,541 | 12/1986 | Moingeon et al. | 204/72 |
| 4,686,018 | 8/1987 | Chaussard | 204/59 R |

*Primary Examiner*—John F. Niebling
*Assistant Examiner*—Steven P. Marquis
*Attorney, Agent, or Firm*—Burns, Doane, Swecker & Mathis

[57] ABSTRACT

The present invention relates to a process for the electrochemical synthesis of alpha-saturated ketones by electrochemical reduction, in an organic solvent medium, of alpha-saturated organic halides in the presence of $CO_2$ and of a catalyst based on nickel complexed with a bidentate organic ligand containing two nitrogen atoms, such as 2,2'-bipyridine and, optionally, with an ethylenic coligand.

The anode, made of a metal chosen from the group consisting of the reducing metals and their alloys, is consumed during the electrochemical reaction whose site it is. It is preferably made of magnesium.

This process is simple to use and allows a single-compartment cell to be employed.

Alpha-saturated ketones are compounds commonly employed in the chemical industry, particularly as solvents or synthesis intermediates.

14 Claims, No Drawings

PROCESS FOR THE ELECTROCHEMICAL SYNTHESIS OF ALPHA-SATURATED KETONES

The invention relates to a process for the electrochemical synthesis of alpha-saturated ketones by electrochemical reduction of alpha-saturated organic halides, a process carried out in an electrolysis cell in an organic solvent medium containing a support electrolyte.

An alpha-saturated ketone means a ketone in which the 2 carbon atoms linked directly to the carbonyl group (that is to say situated alpha to the carbonyl group) are hybridized "sp$^3$" (tetrahedral hybridization). These carbon atoms, also called "saturated" carbon atoms, do not therefore form part of an ethylenic or acetylenic unsaturation or of a ring or an aromatic heterocyclic ring.

Similarly, an alpha-saturated organic halide means an organic halide in which the carbon atom linked directly to the halogen is hybridized "sp$^3$".

Ketones and especially alpha-saturated ketones are compounds which are commonly employed in virtually all the fields of industrial chemistry, especially as solvents or synthesis intermediates.

In Chemistry Letters, 1977, pages 1021–1024, Shono describes the electrosynthesis of benzyl ketones by electrochemical reduction of benzyl chlorides in the presence of carboxylic acid chlorides in an acetonitrile or N,N-dimethylformamide (DMF) medium. The cell necessarily comprises two compartments separated by a ceramic diaphragm and the anode is made of carbon. The chemical and electrochemical yields are fairly low, especially in DMF.

FR No. 2,579,626, to which the Applicant Company holds title, proposes a process which is simpler and which offers higher yields. This result is attained by employing an organic acid anhydride as an organic acid derivative and an anode made of metal chosen from the group consisting of magnesium, zinc, aluminium and their alloys. However, anhydrides are often tricky to handle.

The present invention proposes a process for the electrochemical synthesis of alpha-saturated ketones which is just as simple as that described in FR No. 2,579,626 but used beginning with $CO_2$ and with alpha-saturated organic halides. The use of $CO_2$, a common, cheap and easily handled gas, instead of acid anhydrides or of acid chlorides in the known processes, presents an undoubted practical and economic advantage.

The process according to the invention for the electrosynthesis of alpha-saturated ketones by electrochemical reduction of alpha-saturated organic halides in an electrolysis cell equipped with electrodes in an organic solvent medium containing a support electrolyte is characterized in that the anode is made of a metal chosen from the group consisting of the reducing metals and their alloys and in that the reduction takes place in the presence of $CO_2$ and of a catalyst based on nickel complexed with a bidentate organic ligand containing two nitrogen atoms. "Their alloys" means any alloy containing at least one reducing metal.

The anode is preferably made of a metal chosen from the group consisting of zinc, aluminium, magnesium and their alloys, namely any alloy containing at least zinc, aluminium or magnesium. It is consumed during the electrochemical reduction whose site it is. A process with a consumable anode, also called "with a soluble anode" is therefore involved. In a particularly preferred manner, the anode is made of a metal chosen from the group consisting of magnesium and its alloys, namely alloys containing magnesium.

The alpha-saturated organic halides preferably correspond to the general formula (A):

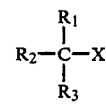

in which

X denotes a halogen atom, preferably chlorine or bromine, and $R_1$, $R_2$ and $R_3$, which are identical or different, denote a hydrogen atom or a substituted or unsubstituted, saturated or unsaturated, aliphatic, aromatic or heterocyclic organic radical, optionally substituted by at least one group which cannot be electrically reduced under the conditions of the electrolysis, such as, for example, an ether, ester or nitrile group, or else $R_1$ and $R_2$ form an aliphatic ring.

In a particularly preferred manner, $R_1$ and $R_2$ denote hydrogen and $R_3$ denotes either a substituted or unsubstituted, saturated or unsaturated hydrocarbon group or an aromatic group such as an optionally substituted phenyl group.

Alkyl chains containing a number of carbon atoms smaller than or equal to 15 may be mentioned as an example of saturated hydrocarbon groups, and vinyl groups as an example of unsaturated hydrocarbon groups.

The preferred organic halides according to the invention are alkyl bromides of the general formula $C_nH_{2n+1}Br$ ($n \leq 15$) and benzyl chlorides or bromides and allyl chlorides or bromides.

According to an alternative form, a single alpha-saturated organic halide is reduced. If this halide is denoted by the formula RX, the symmetrical ketone of formula

is obtained.

According to another alternative form of the invention, electrochemical reduction of a mixture of a number of different alpha-saturated organic halides is carried out. mixture of mixed ketones and of symmetrical ketones is thus obtained.

According to this alternative form, a mixture of 2 different alpha-saturated organic halides is preferably employed. If these 2 halides are denoted by the formulae RX and R'X', a mixture of the following 3 ketones is obtained:

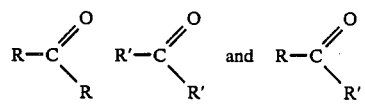

The nickel-based catalyst is obtained by mixing a nickel halide, preferably $NiBr_2$, with a bidentate organic ligand containing two nitrogen atoms. An excess of ligand is preferably employed, for example 1 to 10 moles of ligand per mole of nickel halide.

The bidentate organic ligand containing two nitrogen atoms is preferably 2,2,'-bipyridine. In this case, 2 to 3 moles of ligand are preferably employed per mola of nickel halide.

It has been found, unexpectedly, that markedly superior yields are obtained when the catalyst is obtained in the presence of an ethylenic coligand.

For example, a catalyst of this kind is obtained by using 2,2,'-bipyridine in a proportion of 1 to 1.5 moles per mole of nickel halide and maintaining a partial pressure of ethylene over the solution.

The catalyst concentration in the organic solvent is generally between $10^{-3}$ and $5 \cdot 10^{-2}$ M, preferably between $10^{-2}$ and $2 \cdot 10^{-2}$ M.

The alpha-saturated organic halide or the mixture of alpha-saturated organic halides is preferably added gradually during the reaction, so as to maintain a concentration close to that of the catalyst in the organic solvent.

Unexpectedly, better yields are thus obtained. The total quantity of added halide may reach one mole per liter of solvent, preferably 0.2 to 0.5 mole.

The $CO_2$ pressure is generally between 0.01 MPa and 1 MPa. The work is preferably done at atmospheric pressure (approximately 0.1 MPa).

The cathode is made of any metal such as stainless steel, nickel, platinum, copper, gold, or graphite. It preferably consists of a cylindrical grid or plate arranged concentrically around the anode.

The electrodes are supplied with direct current by means of a stabilized supply.

The organic solvents employed within the scope of the present invention are the low-protic solvents usually employed in organic electrochemistry. Mention may be made, for example, of DMF, acetonitrile, tetramethylurea (TMU), N-methylpyrrolidone (NMP), hexamethylphosphorotriamide (HMPT) and mixtures of these products. DMF or NMP is preferably employed.

The support electrolytes employed to make the medium conductive are those usually employed in organic electrochemistry. There may be mentioned, for example, salts in which the anion is a halide, a perchlorate or a fluoroborate, and the cation a quaternary ammonium, lithium, sodium, potassium, magnesium, zinc or aluminium.

Tetrabutylammonium fluoroborate or tetrabutylammonium bromide is preferably employed.

The concentration of the support electrolyte in the organic solvent is preferably between 0.01 M and 0.5 M.

The cathode current density is preferably chosen between 0.2 and 5 A/dm$^2$. The operation is generally performed at constant current, but it is also possible to operate at constant voltage, at controlled potential, or with variable current and potential.

The invention is illustrated by the examples which are to follow, and which do not imply any limitation. A conventional uncompartmented cell is employed to produce these examples.

The upper part of the cell is made of glass and is equipped with 5 tubes which allow the delivery and exit of gas, optional sampling of the solution during the electrolysis, electrical passages and a passage for the anode by means of a central tube.

The lower part consists of a plug equipped with a seal, screwed onto the glass upper part.

The working volume is approximately 35 cm$^3$.

The anode is a cylindrical rod 0.5 cm in diameter, immersed in the solution over a length of approximately 2 cm. It is in an axial position relative to the cell.

The cathode consists of a grid arranged concentrically around the anode. The working surface of the cathode is of the order of 10 cm$^2$.

The solvent is purified by vacuum distillation.

The solution is stirred by means of a bar magnet and the electrolysis takes place at ambient temperature.

The products obtained are measured, isolated, purified and identified using conventional methods.

EXAMPLE 1—Synthesis of di-n-hexyl ketone.

The cathode is made of old and the anode of magnesium.

30 cm$^3$ of NMP, 3 mmol of tetrabutylammonium fluoroborate, 0.6 mmol of NiBr$_2$ and 1.5 mmol of 2,2,'-bipyridine are introduced into the cell.

The cell is kept under a $CO_2$ atmosphere, with a slight overpressure relative to atmospheric pressure.

This mixture is electrolysed for 40 min with a current of a constant intensity of 0.05 A and then, while the electrolysis is continued, 12 mmol of n-hexyl bromide are added continuously at a rate of 0.9 mmol per hour.

When all the n-hexyl bromide has been added, the electrolysis is stopped. The solution is then hydrolysed with a 1 M aqueous solution of hydrochloric acid and an extraction with pentane is then performed.

After evaporation of the solvents, the organic phase yields a crude product whose analysis by gas phase chromatography (GPC) shows that dihexyl ketone has been obtained in a 70% yield relative to the n-hexyl bromide employed. The product is purified and isolated by chromatography on a silica column and identified by its IR, NMR and mass spectra.

Example 2—Synthesis of di-n-hexyl ketone.

The procedure is as in Example 1, but only 0.7 mmol of 2,2,'-dipyridine are employed and the $CO_2$ is replaced with a 50/50 volume mixture of $CO_2$ and ethylene.

The yield of dihexyl ketone obtained is 90%.

Examples 3 to 7—Synthesis of various alpha-saturated ketones.

The procedure is as in Example 1, but with other alpha-saturated organic halides whose rate of addition is 1.8 mmol/h instead of 0.9 mmol/h.

Table 1, which follows, specifies the halide employed and the yield and the nature of the ketone obtained.

TABLE 1

| EXAMPLE No. | ORGANIC HALIDE | KETONE OBTAINED | YIELD (%) |
| --- | --- | --- | --- |
| 3 | $\phi CH_2Br$ | $(\phi CH_2)_2CO$ | 85 |
| 4 | $\phi CH_2Cl$ | $(\phi CH_2)_2CO$ | 70 |
| 5 | $CH_3-CH=CH-CH_2Br$ | $(CH_3-CH=CH-CH_2)_2CO$ | 70 |
| 6 | $CH_3-CH=CH-CH_2Cl$ | $(CH_3-CH=CH-CH_2)_2CO$ | 40 |

TABLE 1-continued

| EXAMPLE No. | ORGANIC HALIDE | KETONE OBTAINED | YIELD (%) |
|---|---|---|---|
| 7 | (CH$_3$)$_2$C=CH—CH$_2$Cl | ((CH$_3$)$_2$C=CH—CH$_2$)$_2$CO | 30 |

φ denotes C$_6$H$_5$.

Examples 8 to 12—Synthesis of dibenzyl ketone

The procedure is as in Examples 3 and 4, but with modification of the solvent or of the support electrolyte.

Dibenzyl keton is obtained in all these ples. Table 2, which follows, specifies the starting organic halide, the solvent employed, the nature and the quantity of support electrolyte and the yield of dibenzyl ketone obtained expressed relative to the starting organic halide.

TABLE 2

| EXAMPLE No. | ORGANIC HALIDE | SOLVENT | SUPPORT ELECTROLYTE | | YIELD (%) |
|---|---|---|---|---|---|
| 8 | φCH$_2$Br | DMF | NBu$_4$BF$_4$ | (3 mmol) | 33 |
| 9 | φCH$_2$Br | DMF | NBu$_4$Br | (3 mmol) | 77 |
| 10 | φCH$_2$Cl | NMP | NBu$_4$Br | (3 mmol) | 77 |
| 11 | φCH$_2$Cl | NMP | NBu$_4$Br | (1,5 mmol) | 40 |
| 12 | φCH$_2$Br | DMF | NBu$_4$Br | (6 mmol) | 80 |

φ denotes C$_6$H$_5$

Example 13—Synthesis of dibenzyl ketone

The procedure is as in Example 3, but a goldplated nickel cathode is employed. The yield is 76%.

Example 14—Synthesis of dibenzyl ketone.

The procedure is as in Example 9, but a vitreous carbon cathode is employed. The yield is 77%.

Examples 15 to 18—Synthesis of various alpha-saturated ketones.

The procedure followed uses the same conditions as those in Example 1, with other alpha-saturated halides, but with only 0.3 mmol of NiBr$_2$ and 0.75 mmol of 2,2'-bipyridine.

Table 3, which follows, specifies, for each example, the starting halide, and the nature and the yield of the ketone obtained, relative to the starting halide.

TABLE 3

| EXAMPLE No. | ORGANIC HALIDE | KETONE OBTAINED | YIELD (%) |
|---|---|---|---|
| 15 | nC$_7$H$_{15}$Br | (nC$_7$H$_{15}$)$_2$CO | 70 |
| 16 | φCH$_2$Cl | (φCH$_2$)$_2$CO | 70 |
| 17 | CH$_3$CH=CH—CH$_2$Br | (CH$_3$CH=CH—CH$_2$)$_2$CO | 80 |
| 18 | (CH$_3$)$_2$C=CH—CH$_2$Br | ((CH$_3$)$_2$C=CH—CH$_2$)$_2$CO | 50 |

φ denotes C$_6$H$_5$

Example 19—Synthesis of benzyl n-hexyl ketone.

The procedure followed uses the same conditions as those in Example 3, but benzyl bromide is replaced with an equimolar mixture of benzyl chloride and of n-hexyl bromide. The ketone n-C$_6$H$_{13}$COCH$_2$φ is obtained in a 25% yield.

We claim:

1. Process for the electrochemical synthesis of alpha-saturated ketones by the electrochemical reduction of alpha-saturated organic halides in an electrolysis cell equipped with electrones in an organic solvent medium containing a support electrolyte, comprising utilizing an anode made of a metal chosen from the group consisting of the reducing metals and their alloys and performing said reduction in the presence of CO$_2$ and a catalyst based on nickel complexed with a bicentate organic ligand containing two nitrogen atoms.

2. Process according to claim 1, wherein said anode is made of a metal chosen from the group consisting of magnesium and its alloys.

3. Process according to claim 1, wherein said alpha-saturated organic halides correspond to the general formula

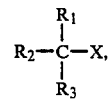

in which
X denotes a halogen atom, and
R$_1$, R$_2$ and R$_3$, which are identical or different, denote a hydrogen atom or a substituted or unsubstituted, saturated or unsaturated, aliphatic, aromatic or heterocyclic organic radical, or said radical is substituted by at least one group which cannot be electrically reduced under the conditions of the electrolysis, or R$_1$ and R$_2$ form an aliphatic ring.

4. Process according to claim 3, when X denotes chlorine or bromine, R$_1$ and R$_2$ are both hydrogen and R$_3$ is a substituted or unsubstituted, saturated or unsaturated hydrocarbon group or an aromatic group.

5. Process according to claim 1 wherein a mixture of at least two alpha-saturated organic halides is reduced.

6. Process according to claim 1, wherein a signal alpha-saturated organic halide is reduced.

7. Process according to claim 1, wherein the nickel-based catalyst is obtained by mixing a nickel halide with a bidentate organic ligand containing two nitrogen atoms.

8. Process according to claim 1, wherein the nickel-based catalyst is obtained in the presence of an ethylenic coligand.

9. Process according to claim 5, wherein said mixture of alpha-saturated organic halides is added gradually during the electrosynthesis.

10. Process according to claim 3, wherein X denotes chlorine or bromine.

11. Process according to claim 1, wherein two alpha-saturated organic halides are reduced.

12. Process according to claim 7, wherein the nickel-based catalyst is obtained by mixing a nickel halide with 2,2,'-bipryidine.

13. Process according to claim 8, wherein said ethylenic coligand is ethylene.

14. Process according to claim 6, wherein said alpha-saturated organic halide is added gradually during the electrosynthesis.

* * * * *